United States Patent [19]
D'Alessio et al.

[11] Patent Number: 5,674,286
[45] Date of Patent: Oct. 7, 1997

[54] BIOABSORBABLE MEDICAL IMPLANTS

[75] Inventors: Keith D'Alessio, Madison; Donald S. Kaplan, Weston; Ross R. Muth, Brookfield; John Kennedy, Stratford, all of Conn.

[73] Assignee: United States Surgical Corporation, Norwalk, Conn.

[21] Appl. No.: 914,437

[22] Filed: Jul. 15, 1992

Related U.S. Application Data

[62] Division of Ser. No. 654,234, Feb. 12, 1991, abandoned.

[51] Int. Cl.$^6$ .............................. A61F 2/02; A61F 2/06; A61F 2/28
[52] U.S. Cl. .................. 623/11; 623/1; 623/16; 623/66
[58] Field of Search ................... 623/11, 16, 66, 623/13, 12; 606/60, 69, 77, 70, 76

[56] References Cited

U.S. PATENT DOCUMENTS

| | | | |
|---|---|---|---|
| 2,703,316 | 3/1955 | Schneider | 260/78.3 |
| 3,297,033 | 1/1967 | Schmitt et al. | 128/335.5 |
| 3,739,773 | 6/1973 | Schmitt et al. | 128/92 R |
| 3,784,585 | 1/1974 | Schmidtt et al. | |
| 3,839,297 | 10/1974 | Wasserman et al. | 260/78.3 R |
| 3,867,190 | 2/1975 | Schmidtt et al. | |
| 3,902,497 | 9/1975 | Casey | 128/296 |
| 4,045,418 | 8/1977 | Sinclair | |
| 4,052,988 | 10/1977 | Doddi et al. | 128/335.5 |
| 4,057,537 | 11/1977 | Sinclair | |
| 4,128,612 | 12/1978 | Roth | 264/126 |
| 4,201,216 | 5/1980 | Mattei | |
| 4,263,185 | 4/1981 | Belykh et al. | 260/17.4 R |
| 4,279,249 | 7/1981 | Vert et al. | 128/92 |
| 4,326,522 | 4/1982 | Guerrero et al. | |
| 4,343,931 | 8/1982 | Barrows | 528/291 |
| 4,357,193 | 11/1982 | McGann et al. | 156/286 |
| 4,429,080 | 1/1984 | Casey et al. | |

(List continued on next page.)

FOREIGN PATENT DOCUMENTS

| | | |
|---|---|---|
| 0011528 | 5/1980 | European Pat. Off. |
| 0146398 | 6/1985 | European Pat. Off. |
| 0204931 | 12/1986 | European Pat. Off. |

(List continued on next page.)

OTHER PUBLICATIONS

Kulkarni et al., J. Biomed, Mater, Res., 1971, 5, pp. 169–181.
Vert et al., Makromol. Chem, Suppl. 1981, 5, 30–41.
Christel et al., Biomaterials, 1980, 271–280.
Jan van Randenborgh, dissertation, University of Wurzburg, 1983.
NASA Tech Brief Fall 1982.
Vasenius, Clinical materials, 4 (1989), pp. 307–317.
Gillett et al.
Zimmerman et al., J. Biomed, Mater, Res.: Applied Biomaterials, vol. 21, No. A3, pp. 345–3612 (1987).
Parsons et al., Composites for Orthopaedics, Chapter 38, pp. 873 to 905 (Section of Orthopaedic Surgery, College of Medicine and Dentistry, New Jersey Medical School).
Tunc, Transactions of the Ninth Annual Meeting of the Society For Biomaterials, Birmingham, U.S.A., 1983, 47.

(List continued on next page.)

Primary Examiner—David J. Isabella

[57] ABSTRACT

A completely bioabsorbable reinforced composite material for use in medical implants and a method for making same. The composite material comprises a hybrid yarn of intimately co-mingled reinforcement fibers of a crystalline polymer and matrix fibers of a polymer having a glass transition temperature below the melting point of the crystalline polymer. The hybrid yarn is heated under pressure to a processing temperature between the glass transition temperature of the matrix fibers and the melting point of the crystalline polymer to form a continuous matrix with reinforcing fibers of crystalline polymer. The composite material may be formed by a two step consolidation process.

8 Claims, 9 Drawing Sheets
(2 of 9 Drawing(s) in Color)

U.S. PATENT DOCUMENTS

| | | |
|---|---|---|
| 4,496,446 | 1/1985 | Ritter et al. . |
| 4,539,249 | 9/1985 | Curzio .................................... 428/175 |
| 4,539,981 | 9/1985 | Tunc ........................................ 128/92 |
| 4,550,449 | 11/1985 | Tunc ........................................ 623/16 |
| 4,590,027 | 5/1986 | Murphy et al. ......................... 264/135 |
| 4,595,713 | 6/1986 | St. John .................................. 523/105 |
| 4,604,097 | 8/1986 | Graves, Jr. et al. ...................... 623/11 |
| 4,610,688 | 9/1986 | Silvestrini et al. ......................... 623/1 |
| 4,612,923 | 9/1986 | Kronenthal ................................ 128/92 |
| 4,620,541 | 11/1986 | Gertzman et al. . |
| 4,624,256 | 11/1986 | Messur et al. . |
| 4,643,734 | 2/1987 | Lin ........................................... 623/16 |
| 4,646,741 | 3/1987 | Smith . |
| 4,655,203 | 4/1987 | Törmälä et al. .......................... 128/92 |
| 4,655,777 | 4/1987 | Dunn et al. . |
| 4,741,337 | 5/1988 | Smith et al. . |
| 4,743,257 | 5/1988 | Törmälä et al. .......................... 623/16 |
| 4,781,183 | 11/1988 | Casey et al. ........................... 623/16 X |
| 4,792,336 | 12/1988 | Hlavacek et al. ......................... 623/13 |
| 4,799,985 | 1/1989 | McMahon et al. ...................... 156/166 |
| 4,800,113 | 1/1989 | O'Connor ................................ 428/175 |
| 4,889,119 | 12/1989 | Jamiolkowski et al. . |
| 4,891,263 | 1/1990 | Kotliar et al. . |
| 4,898,186 | 2/1990 | Ikada et al. ............................... 606/62 |
| 4,905,680 | 3/1990 | Tunc ........................................ 606/69 |
| 4,916,193 | 4/1990 | Tang et al. . |
| 4,916,207 | 4/1990 | Boyle, Jr. et al. . |
| 4,920,203 | 4/1990 | Tang et al. . |
| 4,944,974 | 7/1990 | Zachariades .............................. 428/36.1 |
| 4,960,866 | 10/1990 | Bendix et al. . |
| 4,968,317 | 11/1990 | Törmälä et al. .......................... 606/77 |
| 4,976,909 | 12/1990 | Dorband et al. . |
| 5,061,281 | 10/1991 | Mares et al. ............................. 623/11 |
| 5,064,439 | 11/1991 | Chang et al. ............................. 623/66 |
| 5,066,772 | 11/1991 | Tang et al. . |
| 5,080,665 | 1/1992 | Jarrett et al. ............................. 606/219 |
| 5,084,051 | 1/1992 | Tormala et al. ........................... 606/76 |
| 5,120,802 | 6/1992 | Mares et al. . |
| 5,145,945 | 9/1992 | Tang et al. . |
| 5,152,781 | 10/1992 | Tang et al. . |
| 5,185,408 | 2/1993 | Tang et al. . |

FOREIGN PATENT DOCUMENTS

| | | |
|---|---|---|
| 0239775 | 10/1987 | European Pat. Off. ................. 606/77 |
| 0241252 | 10/1987 | European Pat. Off. ................. 606/77 |
| 0321176 | 6/1989 | European Pat. Off. . |
| 0408898 | 1/1991 | European Pat. Off. . |
| 832405 | 6/1983 | Finland . |
| 1034123 | 6/1966 | United Kingdom . |
| 2181438 | 4/1987 | United Kingdom . |
| WO84/03035 | 8/1984 | WIPO . |
| WO86/07250 | 12/1986 | WIPO . |
| WO89/00431 | 1/1989 | WIPO . |
| WO90/00410 | 1/1990 | WIPO . |
| 9007304 | 7/1990 | WIPO ..................................... 606/70 |
| 9222599 | 12/1992 | WIPO . |

OTHER PUBLICATIONS

AMS, Proceedings of the Fifth International Conference on Polymer in Medicine & Surgery "Resorbable Surg. Devices" Leevuwenhorst Congress Center, Holland, 10th–12th Sep. 1986, pp. 16/1–16/6, London GB PTormala et al.

Webster's II New Riverside University Dictionary, 1984, pp. 906 1167.

Webster's New Collegiate Dictionary, 1977, pp. 885, 1175.

FIG. 20

BIOABSORBABLE MEDICAL IMPLANTS

This is a divisional of application Ser. No. 07/654,234 filed Feb. 12, 1991 now abandoned.

BACKGROUND OF THE INVENTION

1. Field of the Invention

This invention relates to bioabsorbable composite materials for use in medical implants and a method for making same.

2. Background of the Art

It is a common surgical operation to attach a reinforcing rod or plate to a fractured bone so that the broken ends may be stabilized to promote healing. Metal implants have often been used because of their strength. However, it is necessary to perform another operation to remove metal implants after the bone has healed. The metal, being stiffer than the bone, becomes the primary load bearing member thereby protecting the bone from stress. Moderate stress is beneficial to bone tissue, though, and if the metal implant is not removed, the extended stress protection will cause the bone to atrophy through decalcification or osteoporosis. This eventually results in weakening of the bone.

One way to eliminate the necessity of a second operation and the harm of stress protection is to use a bioabsorbable polymer implant. As the bone heals over a period of time, the implant is gradually absorbed by the body and the mechanical stress of daily activity and exercise is gradually reapplied to the bone.

Bioabsorbable materials are also useful for other surgical applications, as for example, in making pins, rods, staples and fasteners for a variety of medical and orthopedic applications. One problem associated with bioabsorbable surgical devices, however, is that the material of construction is not nearly as strong as metal.

Various methods of reinforcement have been evaluated in an attempt to increase the strength of such bioabsorbable implants. One method has been to incorporate a strong non-absorbable fiber or filler, such as carbon fiber, as a reinforcing agent in a bioabsorbable polymer matrix. The disadvantage of such a system is that the non-absorbable fiber remains in the body tissue and may cause histological reaction or other undesirable effects in the long term.

One approach has been to employ a bioabsorbable polymeric material reinforced with a different polymeric material. For example, U.S. Pat. No. 4,279,249 discloses a matrix of polylactic acid or a copolymer thereof reinforced by fibers, threads or other reinforcement elements of polyglyolic acid or a copolymer thereof. The implant is made by providing alternating layers of the polymer constituting the matrix and the reinforcing elements, compressing the layers under pressure at a suitable temperature and then rapidly cooling the composite. Another approach has been to employ self-reinforced bioabsorbable polymeric materials, as described, for example, U.S. Pat. No. 4,743,257. More particularly, U.S. Pat. No. 4,743,257 discloses methods whereby a finely milled polymeric powder is mixed with fibers, threads or corresponding reinforcement units of the same polymeric material or an isomer thereof. In one method, the mixture is heated such that the finely milled particles are softened or melted, but the reinforcement material is not significantly softened or melted. The reinforcement material thus forms a matrix phase which binds the reinforcement units to form a self-reinforced composite. In alternative methods, fibers, threads or corresponding reinforcement units are combined with a polymeric melt of like material, or absorbable fibers, threads or corresponding structures may be heated in a pressurized mold such that the outer surface softens or melts, thereby acting as a matrix.

Despite these known methods, however, a method for producing a bioabsorbable material having suitable in vivo strength and absorption properties in an efficient and controlled manner is needed.

SUMMARY OF THE INVENTION

Provided herein is a method for making a bioabsorbable composite material for use in medical implants. The method comprises placing a plurality of reinforcement fibers and matrix fibers together in close contiguity. The reinforcement fibers comprise a substantially crystalline bioabsorbable polymer characterized by a melting point, and the matrix fibers comprise a bioabsorbable polymer characterized by a glass transition temperature which is lower than the melting point of the reinforcing fiber. The closely placed fibers are then heated under an applied processing pressure to a processing temperature below the melting point of the reinforcement fiber, such that the matrix fibers soften and flow so as to form a matrix around the reinforcement fibers. After being held at the processing temperature and pressure for a period of time sufficient for the matrix fibers to flow around the reinforcement fibers, the resultant reinforcement fiber-containing matrix is permitted to cool. The composite material formed by this process is bioabsorbable and exhibits excellent in vitro strength.

The present invention may further involve formation of the composite material by a two step process wherein the reinforcement and matrix fibers are partially consolidated in a first processing step and then further consolidated in a second processing step.

BRIEF DESCRIPTION OF THE DRAWINGS

The file of this patent contains at least one drawing executed in color. Copies of theis patent with color drawing (s) will be provided by the Patent and Trademark Office upon request and payment of the necessary fee.

DETAILED DESCRIPTION OF THE PREFERRED EMBODIMENTS

The invention described herein is a method for making a completely bioabsorbable reinforced composite material. The material can be used in highly loaded applications and does not suffer from the bio-incompatibility of carbon fiber reinforced materials.

Figure 1:
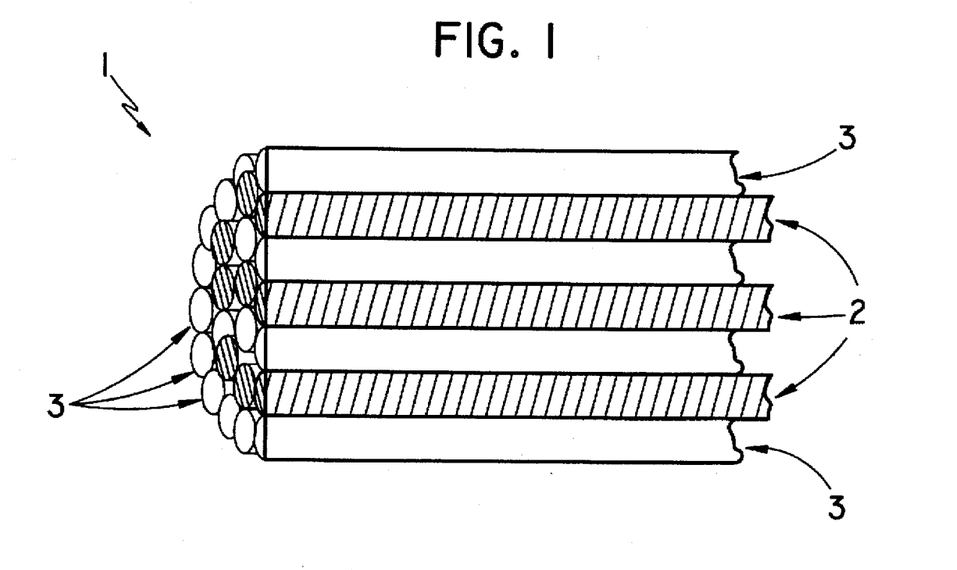
FIG. 1 is a perspective cross-sectional view of the bioabsorbable composite material before being processed.
Figure 2:
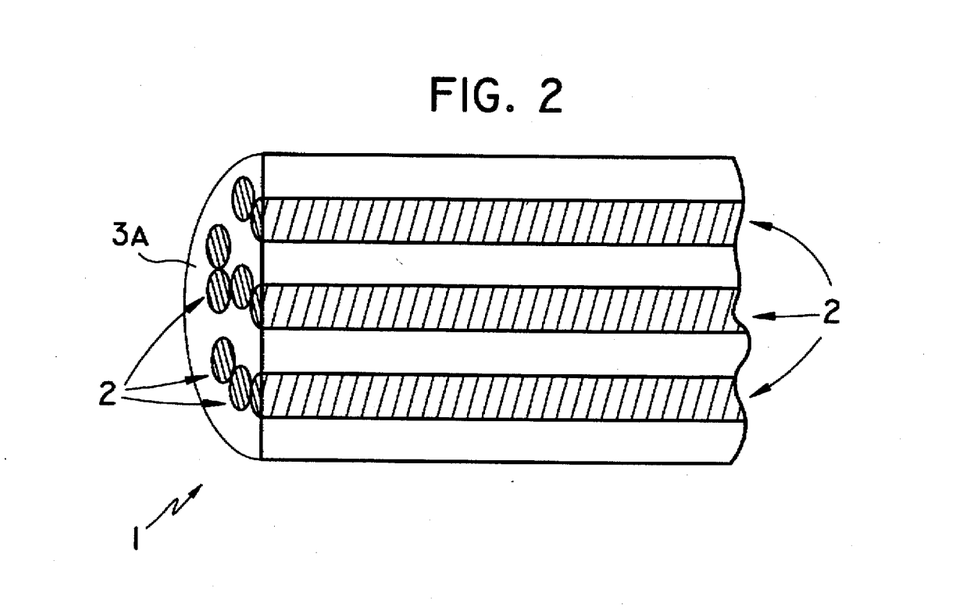
FIG. 2 is a perspective cross-sectional view of the bioabsorbable composite material after being processed.

FIG. 1 illustrates a bundle of fibers or yarn prior to being processed into a bioabsorbable composite material. FIG. 2 illustrates the bioabsorbable composite material prepared in accordance with the method of the present invention. Reinforcing fibers 2 comprise a bioabsorbable polymeric resin such as, for example, a copolymer of polylactic acid (PLA) and polyglycolic acid (PGA). The relative proportion of the components may be chosen to suit the surgical application.

For example, under identical processing conditions, polyglycolic acid is typically the stronger of the two components and more crystalline. However, polyglycolic acid is more rapidly absorbed by body tissue. Hence for surgical applications where it is desired to maintain the implant strength over a longer period of time, the fiber will typically contain more polylactic acid. The fibers can be fibers of the type used in manufacturing suture material.

This invention contemplates that the reinforcing fibers 2 be substantially crystalline. Therefore, the reinforcing material is first spun into fiber form, and then processed to increase its crystallinity, as for example by drawing the fibers as is known in the art to orient the fiber, thereby increasing the crystallinity and strength of the fibers. As used herein, substantially crystalline fibers are characterized by a crystallinity of at least 10% by weight. Being a crystalline fiber, it is thermally stable until the melt temperature of the crystals is achieved.

The matrix fibers 3 are fabricated from a bioabsorbable polymer, copolymer, or blend of polymers and/or copolymers such as polyglycolic acid/polylactic acid copolymer blended with polycaprolactone.

The composition of the matrix fibers 3 includes a bioabsorbable component which has a melting point or glass transition temperature below the processing temperature (i.e. below the melting point of the reinforcing fibers). Suitable relatively low melting point components include polycaprolactone, polytrimethylene carbonate, polydioxanone, polyorthoesters, copolymers of polycaprolactone and lactic acid and/or glycolic acid, copolymers of polytrimethylene carbonate and lactic acid and/or glycolic acid, and copolymers of polydioxanone and lactic acid and/or glycolic acid. The addition of these materials also has been found to improve the impact resistance of articles fabricated therefrom.

A preferred blending component is polycaprolactone, which has a melting point of about 60° C. Thus, for example, at typical processing temperatures for reinforcing and matrix fibers of PGA/PLA copolymers, a low melting point component in the matrix fiber such as polycaprolactone is in a molten state and thereby facilitates flow of the matrix material. Another preferred flow agent is polytrimethylene carbonate.

The matrix fibers may be substantially amorphous and left in the as-spun condition rather than drawn as were the reinforcing fibers. Amorphous polymers are typically characterized by a glass transition temperature rather than a melting point. Above the glass transition temperature the amorphous polymer acts as a highly viscous fluid: it can be made to flow under high pressure. Thus the glass transition temperature of the matrix fibers will be below the melting point of the reinforcing fibers.

The matrix fibers 3 and reinforcing fibers 2 are combined to form a hybrid yarn 1 in which the matrix and reinforcing fibers 2 are intimately co-mingled and in close contiguity. For example, one or more matrix fibers 3 and one or more reinforcing fibers 2 may be plied together. Close physical approximation of the matrix fibers 3 to the reinforcing fibers 2 enables the matrix to flow around and substantially encompass the reinforcement fibers 2 with minimal flow distance. The matrix material is thereby converted from the form of individual fibers 3 to a single mass 3a.

The hybrid yarn can be made into unidirectional tapes, woven broad goods, and roving suitable for filament winding, pultrusion, laminating, braiding, etc. Preferably, the reinforcement material constitutes 50–65% volume % of the hybrid yarn 1. The deniers of the matrix and reinforcing fibers are not critical. Typical matrix fiber deniers range from 60 to 300, and typical reinforcement fiber deniers range from 60 to 300. The relationship of the deniers of the respective fibers is typically from about 1:2 to 2:1 reinforcement fiber 2 to matrix fiber 3, and preferably about 1:1 to 1.5:1.

In a preferred embodiment of the present invention, the hybrid yarn 1 is treated to remove monomer and other impurities prior to processing. This treatment is typically accomplished by heating the hybrid yarn 1 under vacuum until monomer and/or impurities have been removed.

Typical processing conditions for monomer and impurity removal include processing temperatures of from about 75° to about 120° C. and vacuum conditions such that vaporized monomers and/or impurities are exhausted from the system, e.g., pressures of from about 50 to about 150 Torr, optionally with an inert gas purge, e.g., dry nitrogen. The processing time will vary depending on the initial purity of the material being treated and the quantity of such material, but treatment times on the order of approximately 48 hours are typically employed.

After the matrix fibers 3 and reinforcing fibers 2 are combined to form the hybrid yarn 1 and optionally treated to remove monomer impurities, the hybrid yarn 1 is heated to a processing temperature which is above the glass transition temperature of the matrix fibers 3 and below the melting point of the reinforcing fibers 2. Pressure is applied to induce flow of the matrix material such that it surrounds the reinforcing fibers 2, thereby transforming the hybrid yarn 1 into a unitary composite mass.

The processing conditions for the reinforcing and matrix materials described above will depend on the polymeric composition of the individual fibers, and particularly the matrix fibers 3. Thus, for example, if the matrix fibers 3 and reinforcing fibers 2 are 18% PGA, 82% PLA, then the glass transition temperature is approximately 60° C. and the melt temperature is about 160° C. For a hybrid yarn 1 which comprises the aforesaid matrix and reinforcing fibers 2, typical processing conditions include a temperature above about 60° C. and below about 160° C., and typically a temperature of from about 70° C. to about 140° C. Typical processing pressures are from about 0 psig to about 600 psig, and preferably about 300 to about 500 psig and more preferably about 400 psig.

As can readily be seen, the method of the present invention allows processing temperatures far below the melting point of the reinforcing fibers 2. Consequently, this reduces danger of weakening the reinforcing fibers 2 by melting.

After the hybrid yarn 1 has been processed for a sufficient period of time, it is typically cooled to ambient temperature while at the processing pressure. The processing pressure is maintained during the cooling step because as the hybrid yarn 1 is cooled, the fibers have a tendency to shrink. By maintaining pressure, this tendency is inhibited.

As the hybrid yarn 1 cools, the matrix material 3a solidifies. There is no need for a rapid cooling because the processing temperature employed need not approach the melt temperature of the reinforcing fibers 2. Typically, the hybrid yarn 1 of the present invention is force cooled, e.g., by passing air and/or a cooling fluid through the platens of the processing equipment.

The processing time for the hybrid yarn 1 depends on several factors which include the number, mass and geometry of the hybrid yarns 1 being processed, the processing temperature and pressure employed, the compositions of the matrix fibers 3 and reinforcing fibers 2, and the degree to which the hybrid yarn 1 is to be consolidated, i.e., the degree to which void spaces in the hybrid yarn 1 are to be eliminated. Typically, the processing equipment includes a vacuum source to withdraw vapors from the hybrid yarns 1 and to thereby prevent degradation (e.g., due to the presence of impurities or moisture) and to assist in the consolidation thereof.

Although it is possible to produce a finished medical implant in a single processing step according to the present invention, in an alternate process to produce medical implants, and particularly medical implants having non-rectilinear or curved geometries, a two step process can be used. This two step method involves placing a plurality of matrix fibers 3 and reinforcing fibers 2 (hybrid yarn) in close contiguity, processing the hybrid yarn 1 at a processing temperature and pressure, and under vacuum, for a period of time to partially consolidate the hybrid yarn 1, e.g., for from 3 to 10 minutes, cooling the hybrid yarn 1 to ambient temperature, and removing the pressure therefrom. Processing conditions for partial consolidation of the hybrid yarn 1 can include a temperature of from about 60° C. to about 160° C. and an applied mechanical pressure of from about 0 to about 600 psig, preferably about 300 to about 500 psig, and more preferably about 400 psig. The partially consolidated hybrid yarn 1 is then further consolidated in a second processing step. Prior to entering the second processing step, the hybrid yarn 1 may be cut into multiple pieces such that the hybrid yarn 1 may be efficiently placed in a compression mold, e.g., a mold for a pin, rod, or staple, or such that pieces of the yarn may be stacked to form a multiple layer product. The two step process is thus particularly advantageous where the desired medical implant is to be produced in a compression mold. The fact that the hybrid yarn 1 is only partially consolidated upon entering the compression mold allows freer movement of the matrix material relative to the reinforcing fibers 2 than would be possible had the hybrid yarn 1 been fully consolidated in the initial step.

The processing conditions for the second processing step are typically the same as are employed in the initial processing step, although as will be apparent to one of ordinary skill in the art, pressure applied to a part in a compression mold is difficult, if not impossible, to quantify. Total applied mechanical force may be as high as 30,000 pounds.

It is also difficult to quantify the degree to which a hybrid yarn 1 has been consolidated at any given time according to the present invention. Cross-sectional SEM photographs give some indication of the degree to which void spaces exist in a hybrid yarn 1. As used herein, the term "partially consolidated hybrid yarn" means a hybrid yarn that has had a substantial percentage of its void spaces removed, e.g., at least 10% of the original void space eliminated. Typically, the initial processing step is believed to remove from about 30% to about 70% of the void space originally present in the hybrid yarn 1, but as noted above, the percentage is difficult to measure. The second processing step typically removes at least about 10% of the remaining voids in the partially consolidated hybrid yarn.

Figure 3:
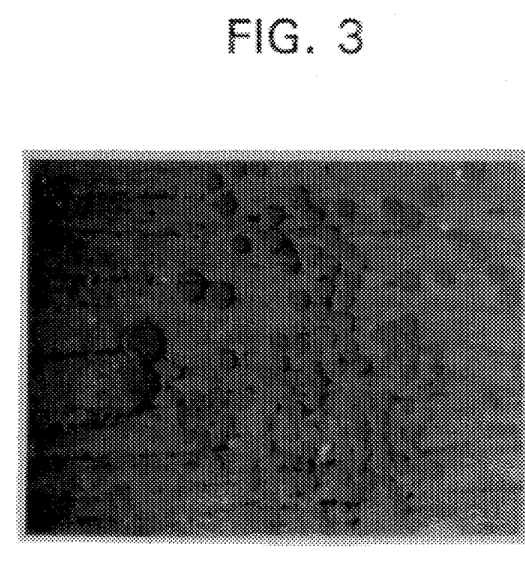
FIGS. 3, 4a and 4b are photomicrographs illustrating cross sections of the hybrid yarn under various degrees of consolidation; and, FIGS. 5 to 20 graphically represent data obtained in the examples below.

FIG. 3 is a photomicrograph showing a cross section of an unconsolidated hybrid yarn at 200× magnification.

Figure 4A:
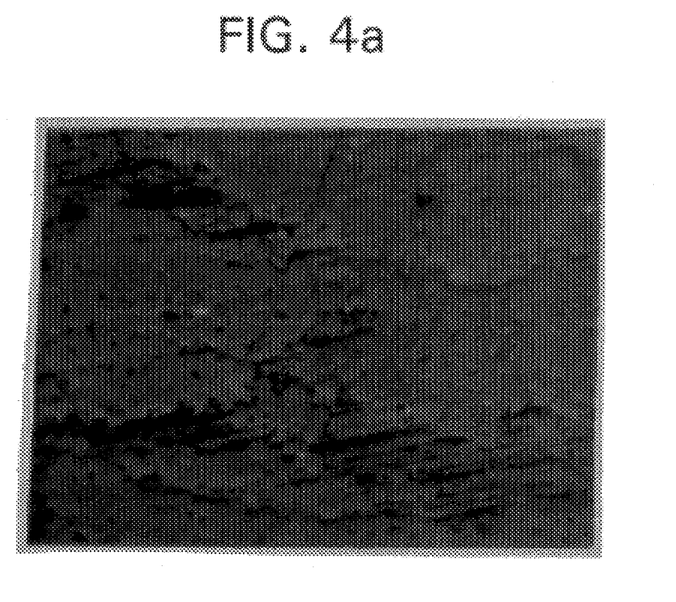

FIG. 4a is a photomicrograph showing a cross section of a partially consolidated hybrid yarn at 200× magnification.

Figure 4B:
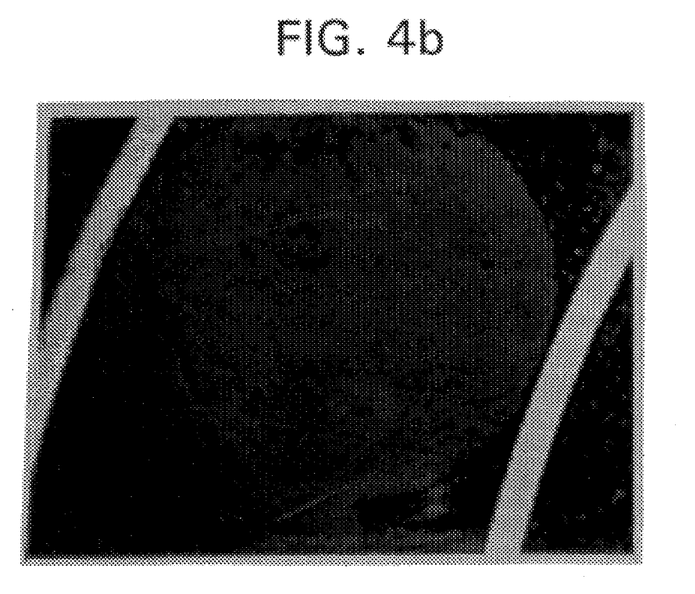

FIG. 4b is a photomicrograph showing a cross section of a pin at 50× magnification after two consolidations.

As can be seen from the above photomicrographs the partial consolidation removes at least some of the void spaces. After two consolidations, void spaces have been removed to a degree such that individual fibers cannot be distinguished.

The description thus far has been directed to the processing of a single hybrid yarn 1 for purposes of clarity. However, the method of the present invention is preferably employed to simultaneously process multiple hybrid yarns 1. Thus, individual hybrid yarns 1 may be oriented unidirectionally, as for example, by winding around an aluminum paddle and by pultrusion or they may be oriented in various directions as for example, by weaving into broad goods, by filament winding, by laminating biased ply lay ups, by braiding, etc. It is also within the scope of the present invention to orient the fibers unidirectionally and transversely at various cross-over angles in one or more succeeding layers.

Any bioabsorbable polymeric material or combination of polymeric materials may be employed as matrix fibers 3 and reinforcement fibers 2 provided a differential exists between the glass transition temperature of the matrix fibers 3 and the melting point of the reinforcement fibers 2. Thus, for example, polymers and copolymers of such synthetic bioabsorbable materials as polylactic acid, polyglycolic acid, polydioxanone, polytrimethylene carbonate, poly(ethylene carbonate), poly(iminocarbonates), polycaprolactone, polyhydroxybutyrate, polyalkylene oxalates, polyalkylene succinates, poly(maleic acid), poly(1,3-propylene malonate), poly(ethylene terephthalate), or poly(amino acids) may be employed. Selection of a suitable absorbable material will depend on such factors as the desired in vivo strength properties and absorption rate for the medical implant being processed.

A further embodiment of the present invention involves the use of matrix fibers of differing composition, e.g., a percentage of individual fibers having a high glycolide content and a percentage of fibers of low glycolide content, or the use of reinforcing fibers of differing composition, or both. The selection of individual matrix and/or reinforcing fiber compositions may be made in such case to achieve the desired absorption rate and tensile strength in the composite material.

The implant material produced according to the present invention is strong, yet completely bioabsorbable. The use of fibers for both the matrix and the reinforcing elements of the hybrid yarn 1 ensures that the matrix and reinforcing elements of the yarn are in close contiguity, and permits efficient and controllable processing of the hybrid yarns 1 into high strength bioabsorbable medical implants. Further details may be derived from the examples below.

EXAMPLE 1

An absorbable composite was manufactured by combining a reinforcement fiber made from a copolymer of 18% glycolic acid and 82% lactic acid with a matrix material consisting of a blend of the above copolymer with 20% polycaprolactone (PCL). The as-spun matrix yarn was 221 denier and the four reinforcement yarns were 87.7 denier. The reinforcement fiber was drawn so as to increase its tenacity and modulus, while the matrix material was utilized in as-spun fiber form. The two yarns were then co-wound onto a flat aluminum paddle. The reinforcement yarn represented 61.1% of the material by volume. The paddle was then compression molded in a vacuum press for about 5 minutes at 110° C. and approximately 400 psi pressure to facilitate flow of the matrix material about the reinforcement fibers. The fiber was then cooled to ambient temperature. The temperature of the processing is below the melt temperature of the reinforcement fibers. The resultant material was a unidirectional reinforced thermoplastic material suitable for the manufacture of a variety of medical products.

EXAMPLE 2

An absorbable composite was manufactured by combining a drawn reinforcement fiber multifilament yarn made from a copolymer of 18% glycolic acid and 82% lactic acid and an as spun fiber of the same material. Five spools of drawn reinforcement fibers having an average denier of 85.4 each were combined with one as-spun yarn of 338.8 denier. The reinforcement fiber constituted 56.6% of the material by volume. The material was wrapped onto a flat aluminum paddle and consolidated at 110° C. and approximately 400 psi pressure. The result was a unidirectional reinforced thermoplastic material suitable for laminating.

EXAMPLE 3

Figure 5:
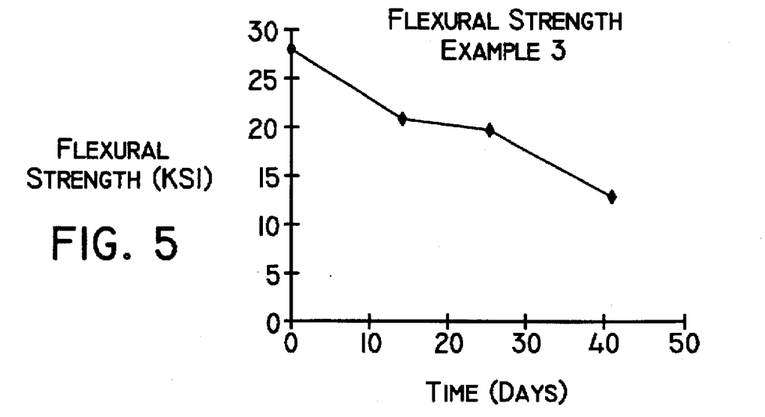
Figure 6:
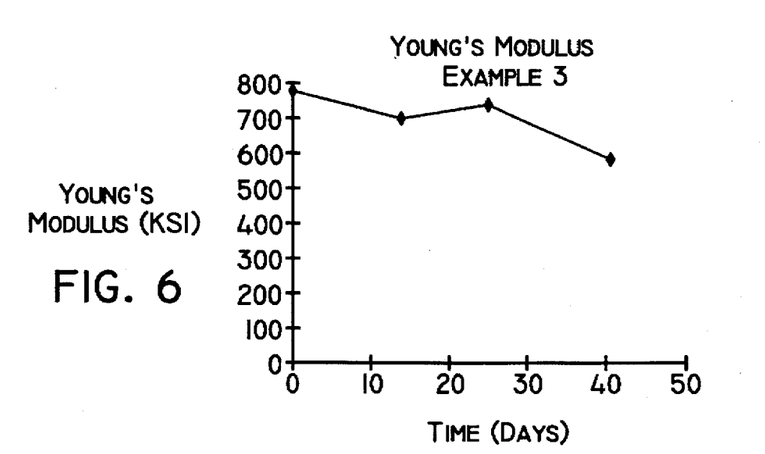
Figure 7:
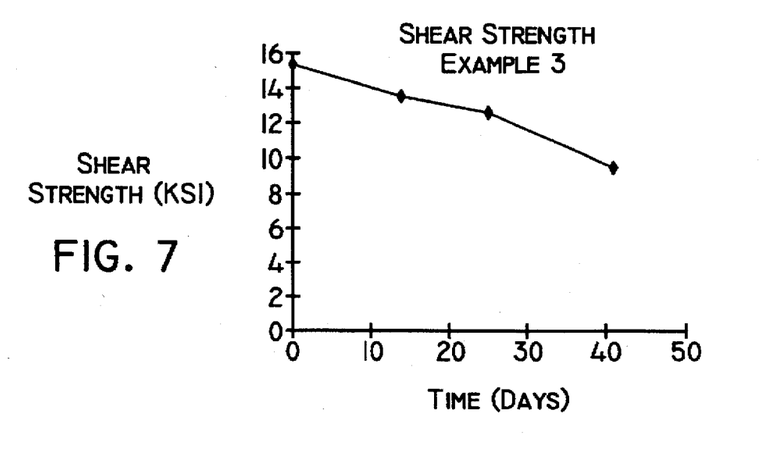

Two laminae of Example 1 are stacked one upon the other and placed in a compression mold with a cylindrical cavity of 0.051" diameter and 2.0" length. The mold was placed into a vacuum press molded at 110° C. for five minutes under 20,000 lbs. of force, and cooled to 30° C. while under pressure. The cylindrical pins were tested in flexure and shear with the following results: Young's Modulus—769.5 Ksi, Flexural Strength—28.0 Ksi, Shear Strength—15.4 Ksi. For comparison purposes an injection molded pin of a copolymer consisting of 18% glycolic acid and 82% lactic acid was similarly tested with the following results: Young's Modulus—466.2 Ksi, Flexural Strength—19.1 Ksi, Shear Strength—7.6 Ksi. Several pins were molded at 110° C. then placed in buffered solution for in vitro testing. The results can be seen in FIGS. 5, 6 and 7.

All flexural tests for this and succeeding examples were accomplished using four point bend configuration with a 16:1 span to depth ratio, a 3:1 span to load nose ratio, and a cross head rate of 0.50"/min. All shear testing was accomplished using a double shear fixture which sheared the pin across its cross section, at 0.20 inches per minute.

EXAMPLE 4

Figure 8:
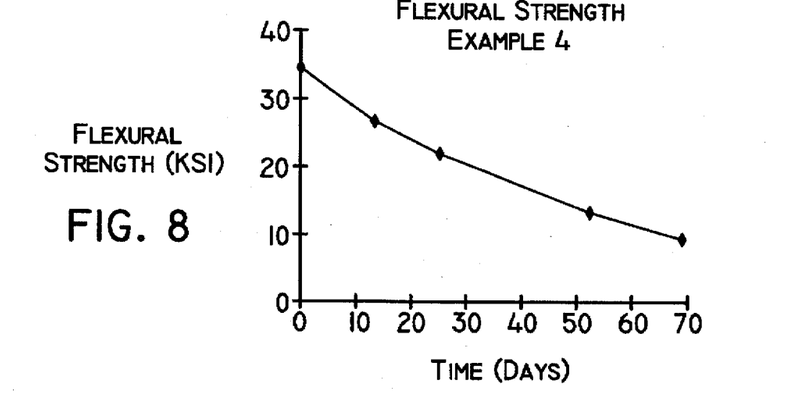
Figure 9:
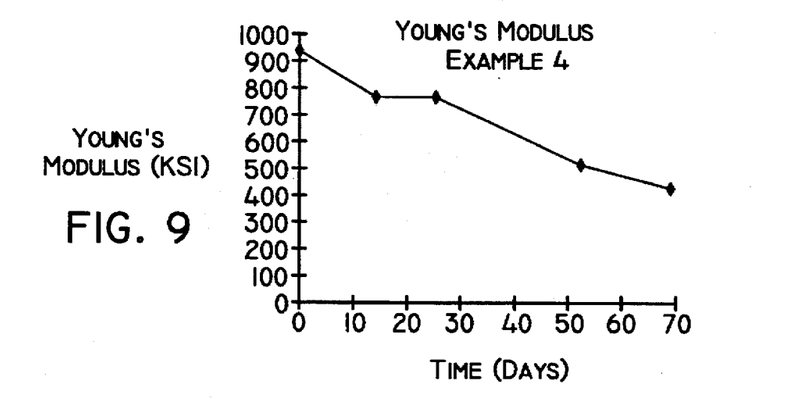
Figure 10:
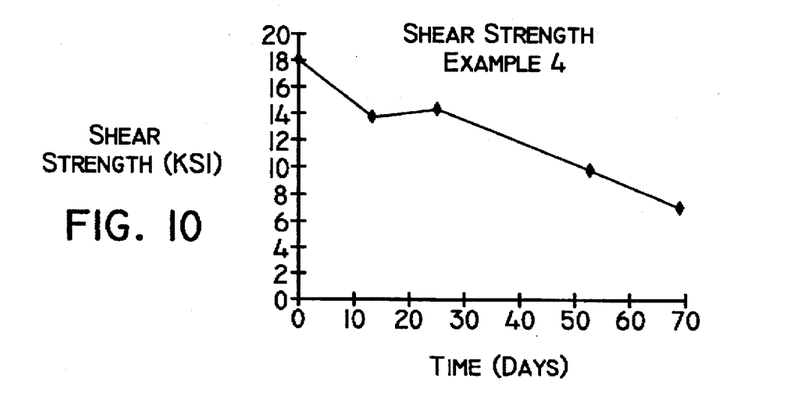

Two laminae of Example 2 were stacked one upon the other and placed in a compression mold with a cylindrical cavity of 0.051" diameter and 2.0" length. The cylindrical pins were tested in flexure and shear with the following results: Young's Modulus—928.1 Ksi, Flexural Strength—34.1 Ksi, Shear Strength—18.1 Ksi. For comparison purposes an injection molded pin of a copolymer consisting of 18% glycolic acid and 82% lactic acid was similarly tested with the following results: Young's Modulus—466.2 Ksi, Flexural Strength—19.1 Ksi, Shear Strength—7.6 Ksi. Several pins were molded at 110° C. then placed in buffered solution for in vitro testing. The results can be seen in FIGS. 8, 9 and 10.

EXAMPLE 5

Two laminae of Example 2 were placed one upon the other in a compression mold with a rectangular cavity with complicated end geometries. The material was molded at 110° C. with pressure in order to demonstrate molding characteristics. The part was later tested in flexure. The Young's Modulus was determined to be 1.191 Msi and the specimen withstood 18.5 Ksi flexural stress without yielding.

EXAMPLE 6

An absorbable composite was manufactured by combining a drawn reinforcement fiber multifilament yarn made from a copolymer of 18% glycolic acid and 82% lactic acid and an as spun fiber multifilament yarn manufactured from a blend consisting of 75% of the above copolymer and 25% polycaprolactone. The reinforcement fiber constituted 53.6% by weight of the total composite yarn. The composite yarn was then wrapped onto an aluminum plate, partially consolidated at 500 psi and 110° C. and later laminated and compression molded into small pins measuring 0.051" in diameter and 2.0" in length.

A second batch of the material was manufactured as described above, with the exception that the wound aluminum paddle was subjected to a monomer/impurity removal treatment cycle ("post treatment") of 110° C. and partial vacuum of 80 Torr, with a 6 cfm flow of dry nitrogen for a period of 48 hours in order to remove residual monomers from the material. After post treatment, the paddle was partially consolidated and small pins were compression molded as described above.

Figure 11:
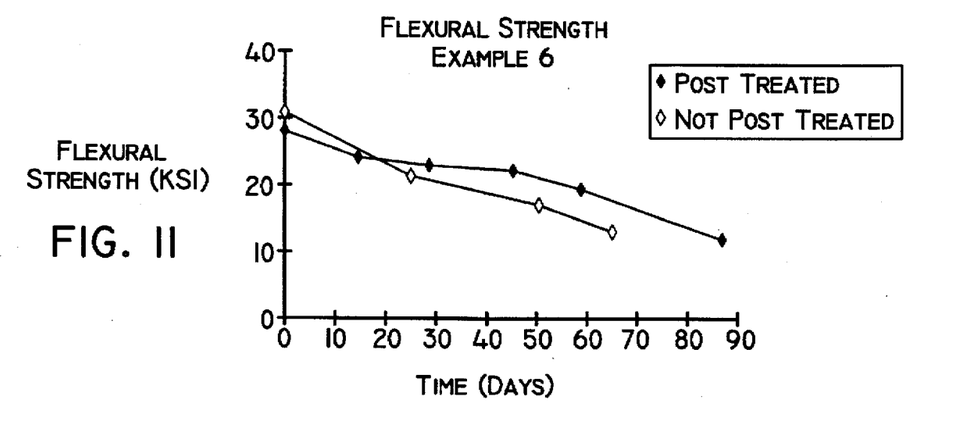
Figure 12:
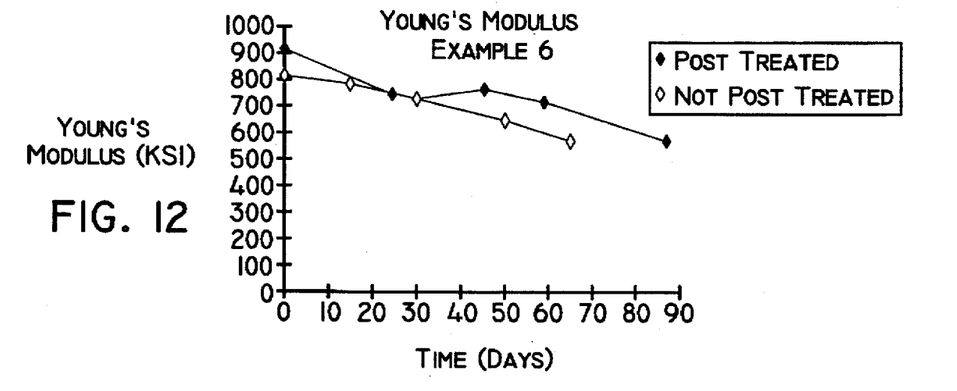
Figure 13:
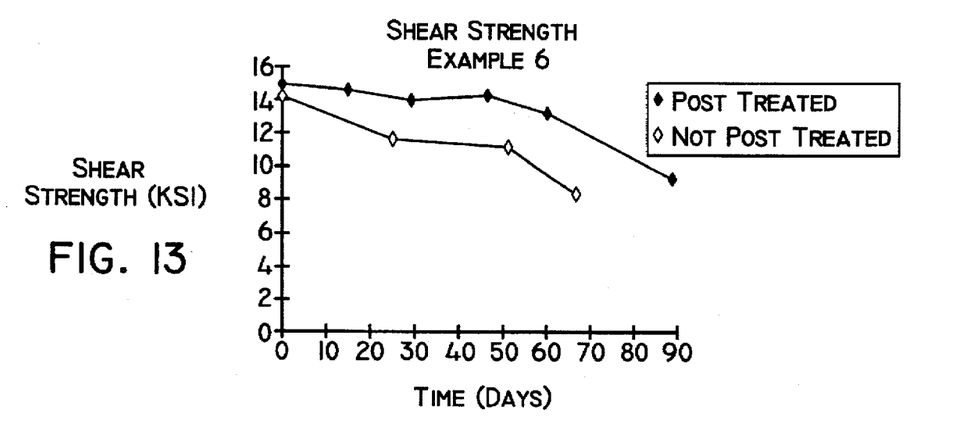

Both sets of pins were then placed in buffered solution for in Vitro testing. The results can be seen in FIGS. 11, 12 and 13.

EXAMPLE 7

An absorbable composite was manufactured by combining a drawn reinforcement fiber multifilament yarn made from a copolymer of 18% glycolic acid and 82% lactic acid and an as spun fiber multifilament yarn manufactured from the same copolymer. The reinforcement fiber constituted 54.8% by weight of the total composite yarn. The composite yarn was then wrapped onto an aluminum plate, partially consolidated at 500 psi and 110° C. and later laminated and compression molded into small pins measuring 0.051" in diameter and 2.0" in length.

A second batch of the material was manufactured as described above, with the exception that the wound aluminum paddle was subjected to a monomer/impurity removal treatment cycle ("post treatment") of 110° C. and partial vacuum of 80 Torr with 6 cfm flow of dry nitrogen for a period of 48 hours in order to remove residual monomers from the material. After post treatment, the paddle was partially consolidated and small pins were compression molded as described above.

Figure 14:
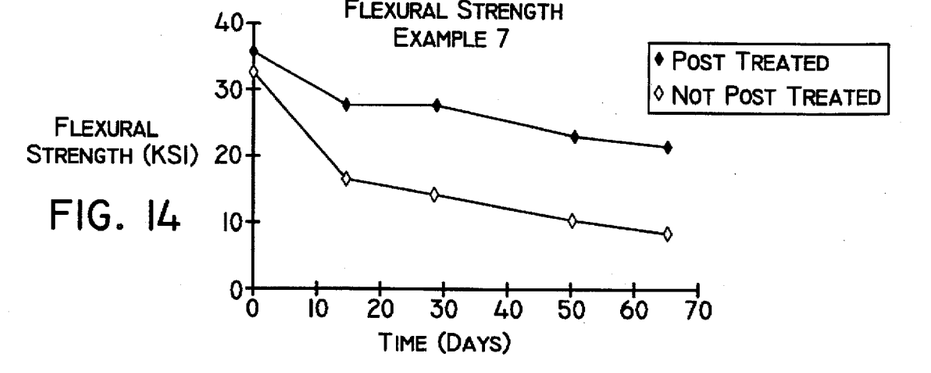
Figure 15:
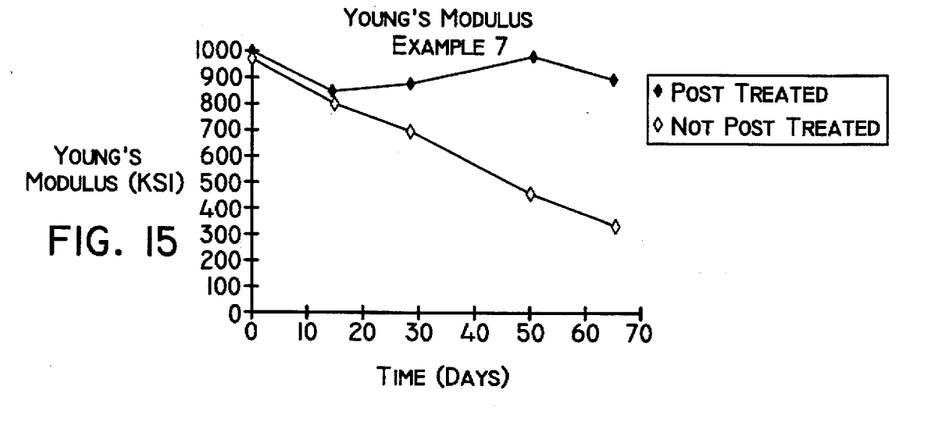
Figure 16:
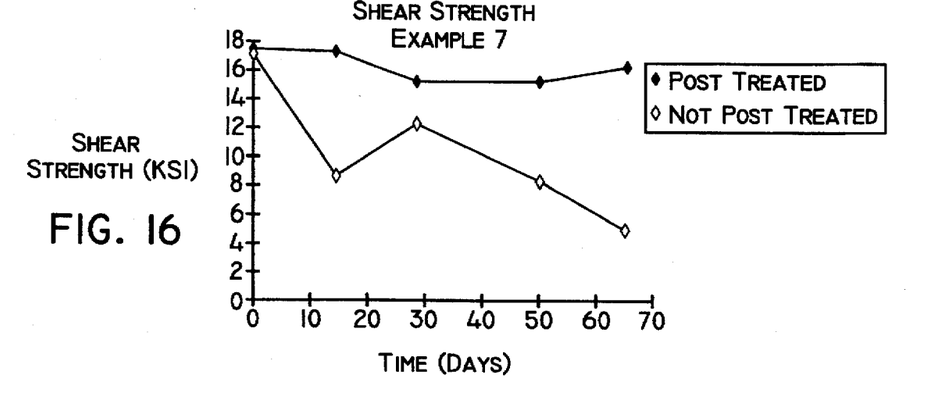
Figure 17:
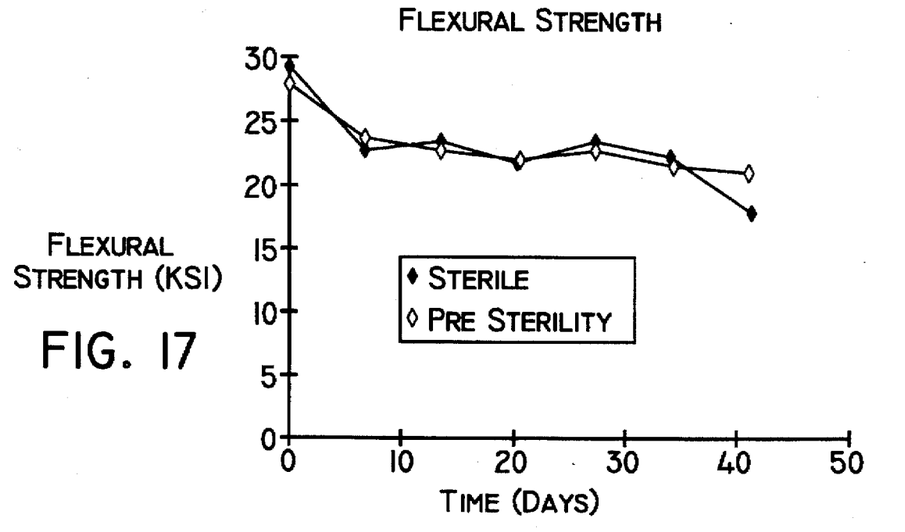
Figure 18:
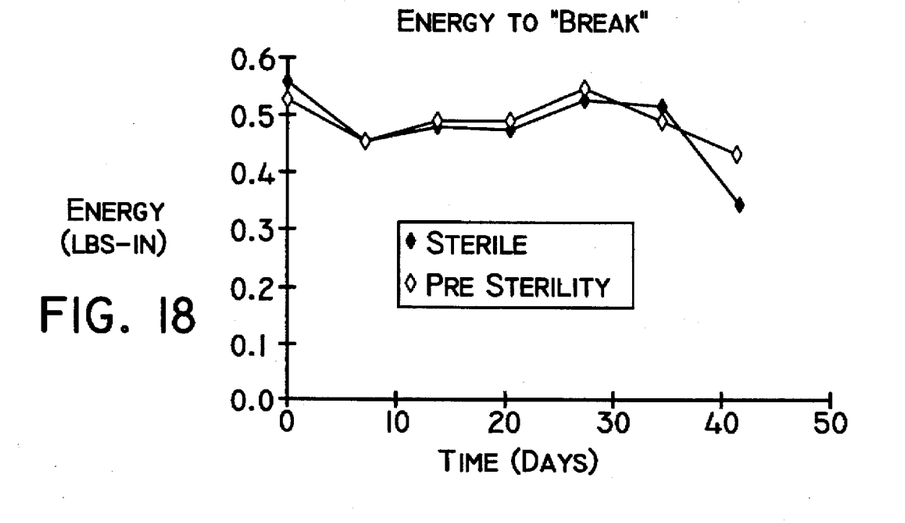
Figure 19:
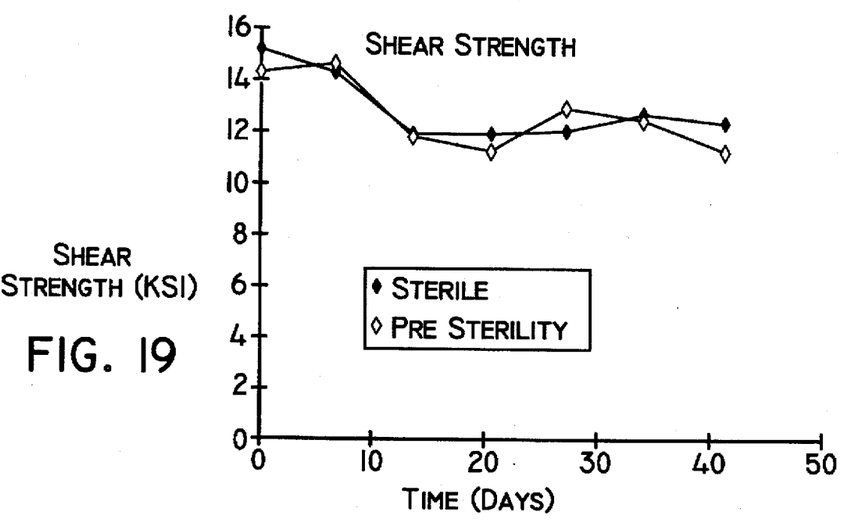
Figure 20:
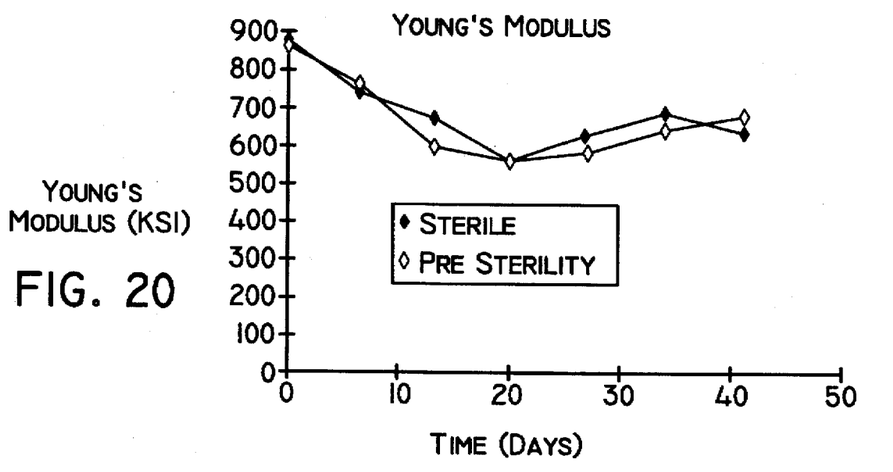

Both sets of pins were then placed in buffered solution for in Vitro testing. The results can be seen in FIGS. 14, 15 and 16.

EXAMPLE 8

An absorbable composite was manufactured as follows: The matrix material was made of an as spun yarn consisting of a blend of 80% trimethylene carbonate and 20% lactic acid copolymer introduced into a copolymer of 18% glycolic acid and 82% lactic acid in a ratio of 25% to 75% respectively. This as spun multifilament yarn was combined with four yarns of drawn reinforcement material consisting of a copolymer of 18% glycolic acid and 82% lactic acid and then wound around an aluminum paddle. The reinforcement material constituted 56.0% weight of the total hybrid yarn. The wound paddle was post treated to remove monomers and vacuum compression molded at 110° C. into partially consolidated flat stock. Two pieces of the resulting material were placed in each cylindrically shaped mold cavity and the entire mold was likewise vacuum compression molded at 110° C. to form pins measuring 0.052 in diameter and 3.5" in length.

The pins were then cut to a length of approximately 1.5". Several pins were ETO (ethylene oxide) sterilized and then placed in Sorenson's Buffer solution at 37° C. while another set of pins were placed directly in Sorenson's Buffer solution at 37° C. without sterilization. The results can be seen in FIGS. 17, 18, 19 and 20 showing the sterilized and non-sterilized pins.

What is claimed is:

1. A bioabsorbable composite surgical implant comprising a hybrid yarn of plied reinforcing and matrix fibers, the reinforcing fibers being made of a bioabsorbable crystalline polymer characterized by a melting point and the matrix fibers being made of a bioabsorbable polymer characterized by a glass transition temperature below the melting point of the crystalline polymer, said hybrid yarn being heated under pressure to a processing temperature above the glass transition temperature of the matrix fibers and below the melting point of the crystalline polymer.

2. The bioabsorbable composite material of claim 1, wherein reinforcing fiber is spun from a polymer selected from the group consisting of polylactic acid, polyglycolic acid, polydioxanone, polytrimethylene carbonate, poly(ethylene carbonate), poly(iminocarbonates), polycaprolactone, polyhydroxybutyrate, polyalkylene oxalates, polyalkylene succinates, poly(maleic acid), poly(1,3-propylene malonate), poly(ethylene terephthalate), poly(amino acids), and copolymers thereof.

3. The bioabsorbable composite material of claim 1, wherein said bioabsorbable polymers of said matrix fibers are substantially amorphous.

4. The bioabsorbable composite material of claim 1, wherein the bioabsorbable polymer of said matrix fibers contain a bioabsorbable component having a melting point below said processing temperature.

5. The bioabsorbable composite material of claim 4, wherein said component is selected from the group consisting of polycaprolactone, polytrimethylene carbonate, polydioxanone, polyorthoesters, copolymers of caprolactone and at least one comonomer selected from the group consisting of and lactic acid and glycolic acid, copolymers of trimethylene carbonate and at least one comonomer selected from the group consisting of lactic acid and glycolic acid, and copolymers of dioxanone and at least one comonomer selected from the group consisting of lactic acid and glycolic acid.

6. The bioabsorbable composite material of claim 4, wherein said hybrid yarn is treated to remove at least one compound selected from the group consisting of monomers and impurities before said hybrid yarn is heated to the processing temperature.

7. The bioabsorbable composite material of claim 6, wherein said treatment to remove at least one compound selected from the group consisting of monomers and impurities comprises heating said hybrid yarn to a temperature from about 75° C. to 120° C. under at least a partial vacuum for a period of time sufficient to remove a substantial amount of the compounds.

8. A bioabsorbable composite surgical implant comprising a hybrid yarn of plied reinforcing and matrix fibers, the reinforcing fibers being made of a bioabsorbable crystalline polymer characterized by a melting point and the matrix fibers being made of a blend of bioabsorbable polymers characterized by a glass transition temperature below the melting point of the crystalline polymer, said hybrid yarn being heated under pressure to a processing temperature above the glass transition temperature of the matrix fibers and below the melting point of the crystalline polymer.

* * * * *